(12) United States Patent
Biatry et al.

(10) Patent No.: US 6,531,160 B2
(45) Date of Patent: Mar. 11, 2003

(54) MICROCAPSULES WITH AN AQUEOUS CORE CONTAINING AT LEAST ONE WATER-SOLUBLE COSMETIC OR DERMATOLOGICAL ACTIVE PRINCIPLE AND COSMETIC OR DERMATOLOGICAL COMPOSITIONS CONTAINING THEM

(75) Inventors: Bruno Biatry, Vincennes (FR); Eric Lheureux, Montgeron (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/849,514

(22) Filed: May 7, 2001

(65) Prior Publication Data

US 2002/0022038 A1 Feb. 21, 2002

(30) Foreign Application Priority Data

May 5, 2000 (FR) .............................. 00 05756

(51) Int. Cl.$^7$ .............................. A61K 9/16; A61K 9/50; A61K 7/42; A61K 7/06; A61K 9/48
(52) U.S. Cl. ................. 424/490; 424/59; 424/70.8; 424/401; 424/451; 424/455; 424/457; 424/489; 424/494; 424/497; 424/498; 424/501; 424/502
(58) Field of Search ................. 424/401, 451, 424/455, 457, 489, 490, 494, 497, 498, 501, 502, 59, 70.8

(56) References Cited

U.S. PATENT DOCUMENTS

| | | | | |
|---|---|---|---|---|
| 3,523,906 A | | 8/1970 | Vrancken et al. ............ 252/316 |
| 3,523,907 A | | 8/1970 | Vrancken et al. ............ 252/316 |
| 4,107,071 A | | 8/1978 | Bayless ....................... 252/316 |
| 4,460,563 A | | 7/1984 | Calanchi ...................... 424/35 |
| 4,857,335 A | * | 8/1989 | Bohm .......................... 424/440 |
| 4,933,105 A | * | 6/1990 | Fong ............................ 264/12 |
| 5,140,043 A | * | 8/1992 | Darr et al. ................... 514/474 |
| 5,154,762 A | | 10/1992 | Mitra et al. .................. 106/35 |
| 5,238,714 A | | 8/1993 | Wallace et al. ........ 427/213.36 |
| 5,589,194 A | | 12/1996 | Tsuei et al. .................. 424/497 |
| 5,767,107 A | | 6/1998 | Chaundy et al. ............. 514/54 |
| 6,197,813 B1 | * | 3/2001 | Hegenauer ................... 514/474 |
| 6,251,313 B1 | * | 6/2001 | Deubzer et al. ............. 264/4.1 |
| 6,348,218 B1 | * | 2/2002 | Hed et al. ................... 424/401 |

FOREIGN PATENT DOCUMENTS

| | | |
|---|---|---|
| DE | 198 02 644 | 7/1999 |
| EP | 0 190 833 | 8/1986 |
| EP | 0 273 890 | 7/1988 |
| EP | 0 316 054 | 5/1989 |
| EP | 0 576 377 | 12/1993 |
| EP | 0 600 775 | 6/1994 |
| FR | 2 245 335 | 4/1975 |
| GB | 1 297 476 | 11/1972 |
| JP | 64-43343 | 2/1989 |
| JP | 405148128 A * | 6/1993 |
| JP | 5-285210 | 11/1993 |
| JP | 8-325117 | 12/1996 |
| WO | 90/13361 | 11/1990 |
| WO | 91/01801 | 2/1991 |
| WO | 94/23832 | 10/1994 |
| WO | 95/27488 | 10/1995 |
| WO | 95/28149 | 10/1995 |

OTHER PUBLICATIONS

Microencapsulation, Methods and Industrial Application; edited by Simon Benita; Drugs and the Pharmaceutical Sciences; vol. 73; 1996.

\* cited by examiner

*Primary Examiner*—Jose' G. Dees
*Assistant Examiner*—Marina Lamm
(74) *Attorney, Agent, or Firm*—Jacobson Holman PLLC

(57) ABSTRACT

The present invention relates to microcapsules with an aqueous core containing at least one water-soluble cosmetic or dermatological active principle, and with a polymeric and/or waxy envelope, in which the said envelope consists

- of at least one polymer chosen from polycaprolactone, poly(3-hydroxybutyrate), poly(ethylene adipate), poly (butylene adipate), cellulose esters of at least one $C_1$–$C_4$ carboxylic acid, copolymers of styrene and of maleic anhydride, copolymers of styrene and of acrylic acid, styrene-ethylene/butylene-styrene block terpolymers, styrene-ethylene/propylene-styrene block terpolymers and terpolymers of ethylene, of vinyl acetate and of maleic anhydride, and/or
- of at least one wax chosen from beeswax, polyglycerolated beeswax, hydrogenated plant oils, paraffin with a melting point above 45° C., and silicone waxes.

24 Claims, No Drawings

MICROCAPSULES WITH AN AQUEOUS CORE CONTAINING AT LEAST ONE WATER-SOLUBLE COSMETIC OR DERMATOLOGICAL ACTIVE PRINCIPLE AND COSMETIC OR DERMATOLOGICAL COMPOSITIONS CONTAINING THEM

The present invention relates to microcapsules with an aqueous core containing at least one water-soluble cosmetic or dermatological active principle, to cosmetic or dermatological compositions containing them and to a process for preparing such microcapsules.

The microencapsulation of cosmetic or dermatological active agents to allow better storage and/or sustained and controlled release is known.

Microencapsulation processes and the principles upon which they are based are described in detail, for example, in <<Microencapsulation, Methods and Industrial Application>>, edited under the direction of Benita, M. Dekker, 1996.

All these processes are based on the use of polymers as constituent elements of the wall of the microparticle which isolates the active agent from the external medium. These microparticles make it possible to encapsulate higher levels of water-soluble active agents than do other vesicular systems such as liposomes, which are nanoparticles formed from phospholipid bilayers surrounding an aqueous core.

It has thus been sought to encapsulate various hydrophilic active agents. Among these, ascorbic acid is of most particular interest, since its instability in aqueous medium makes it difficult to formulate in cosmetic compositions, although it has many beneficial properties.

Specifically, on account of its chemical structure ($\alpha$-keto lactone), ascorbic acid is highly sensitive to certain environmental parameters such as light, oxygen or water. This results in a rapid degradation of the ascorbic acid formulated in the presence of these agents. This instability is liable to impair its efficacy, although it is an active agent of choice for stimulating the synthesis of connective tissue and in particular of collagen, for reinforcing skin tissue defenses against external attack such as ultraviolet radiation and pollution, for compensating for a vitamin E deficiency of the skin, for depigmenting the skin and for trapping free radicals. In particular, these properties make it an excellent candidate as a cosmetic or dermatological active agent for combating or preventing ageing of the skin.

Among the techniques for encapsulating hydrophilic active principles such as ascorbic acid, in dissolved, dispersed or pulverulent form, mention may be made of coacervation (JP-8 325 117, JP-5 285 210 and U.S. Pat. No. 4,460,563), spray-drying (U.S. Pat. No. 5,767,107), air-bed fluidization (WO 95/27488 and EP 0 600 775) or interfacial polymerization (JP 1 043 343, WO 91/01801 and WO 94 23832).

The main drawback of spray-drying and air-bed fluidization is that of encapsulating the active agent in the form of powder, i.e. in solid form. Now, it is often essential in cosmetics or dermatology to encapsulate the active agent in dissolved form in an aqueous medium to ensure its immediate bioavailability to the skin.

The techniques of coacervation or of interfacial polymerization are not suitable for the microencapsulation of water-soluble cosmetic or dermatological active principles since they generally involve the use of polymerizable or bifunctional reagents that are toxic to the skin and liable to react with the active agent to be encapsulated and deactivate it.

Another microencapsulation process has also been used to encapsulate dissolved hydrophilic active agents in microparticles. This is the <<multiple emulsion-solvent evaporation or extraction>> technique, which consists in preparing a water-in-oil primary emulsion by dispersing an aqueous solution of the active principle in an organic solution of a water-insoluble polymer, followed by dispersing this primary emulsion in an outer aqueous phase, in a second stage. The organic solvent is then removed by evaporation or extraction.

This process is disclosed in U.S. Pat. Nos. 3,523,906, 3,523,907, EP 190 833 and WO 95/28149.

U.S. Pat. Nos. 3,523,906 and 3,523,907 disclose, respectively, a multiple emulsion-evaporation process and a multiple emulsion-extraction process using, as polymers constituting the wall of the microcapsules, vinyl polymers or copolymers, polycondensates such as polycarbonates, polyesters, polysulphonates, polyurethanes or polyamides, or natural polymers such as chlorinated natural rubber or cellulose derivatives.

Patent application EP 190 833 discloses a process for encapsulating water-soluble active principles by multiple emulsion-solvent evaporation using water-insoluble biocompatible polymers, and in particular polymers based on lactic acid and on glycolic acid.

Patent application WO 95/28149 discloses the preparation, via a multiple emulsion-evaporation process, of microcapsules having a wall consisting of a copolymer of poly(lactide-co-glycolide) type.

Now, the Applicant has found that the polymers mentioned in the above documents are not suitable for stabilizing active principles either because their hydrolysis in aqueous medium is reflected by the release of organic acids which modify the pH of the composition, or because they do not allow satisfactory degrees of encapsulation to be obtained.

The problem underlying the present invention is consequently that of developing novel microcapsules which contain, in their envelope, polymers that are stable in aqueous medium and produce satisfactory degrees of encapsulation of water-soluble active principles.

Another problem—which is specific to the encapsulation of cosmetic active principles—is associated with the presence of water in cosmetic compositions.

Specifically, the presence of an aqueous phase outside the microcapsules necessitates excellent impermeability of the wall of these microcapsules in order to prevent the active principle from passing into the outer aqueous phase, which would negate all the benefits of the encapsulation. Thus, in the cosmetic field, microcapsules with an impermeable wall which release the active principle only after application, for example following the rupture or biodegradation of the envelope, are generally sought.

This problem does not arise in the pharmaceutical field, in which the microcapsules are generally kept in dried form and need to release the active principle rapidly after they have been placed in contact with an aqueous medium.

The Applicant has discovered that it is possible to solve the problems listed above, i.e. to obtain, with satisfactory degrees of encapsulation, microcapsules consisting of an envelope containing an aqueous solution of at least one stabilized cosmetic or dermatological active principle by appropriately selecting the materials forming the envelope from certain polymers and/or certain waxes.

A subject of the present invention is thus microcapsules with an aqueous core containing at least one water-soluble cosmetic or dermatological active principle, and with a polymeric and/or waxy envelope consisting of at least one polymer chosen from polycaprolactone, poly(3-hydroxybutyrate), poly(ethylene adipate), poly(butylene adipate), cellulose esters of at least one $C_1$–$C_4$ carboxylic acid, preferably mixed cellulose esters of two types of carboxylic acid, copolymers of styrene and of maleic anhydride, copolymers of styrene and of acrylic acid, styrene-ethylene/butylene-styrene block terpolymers, styrene-ethylene/propylene-styrene block terpolymers and terpolymers of ethylene, of vinyl acetate and of maleic anhydride, and/or of at least one wax chosen from beeswax, polyglycerolated beeswax, hydrogenated plant oils, paraffin with a melting point above 45° C., and silicone waxes.

For the purpose of the present invention, a wax is a lipophilic compound which is solid at room temperature (about 25° C.), undergoes a reversible solid/liquid change of state, has a melting point above about 40° C., which may be up to 200° C., and has an anisotropic crystal organization in the solid state.

Silicone waxes which may be mentioned, for example, are alkyl- or alkoxydimethicones containing from 16 to 45 carbon atoms, for example behenoxydimethicone and alkyl esters of $C_{16}$–$C_{45}$ dimethiconol, for instance dimethiconol behenate.

The subject of the present invention is also cosmetic or dermatological compositions containing, in a physiologically acceptable support, microcapsules with an aqueous core and with a polymeric and/or waxy envelope above.

A subject of the present invention is also a process for manufacturing microcapsules with an aqueous core and with a polymeric and/or waxy envelope, which are described above, by multiple emulsification-solvent evaporation.

The microcapsules according to the present invention make it possible to obtain degrees of encapsulation of water-soluble active principles of at least 70%, or even greater than 95%, relative to the weight of the active agent used.

These microcapsules have the advantage of limiting the loss of the hydrophilic active principles encapsulated.

In one embodiment of the invention, the envelope is formed by one or more of the polymers listed above combined with at least one wax chosen from those mentioned above.

These waxes are dissolved together with the organosoluble polymers used according to the present invention in the organic solvent before preparing the primary emulsion.

The active agent to be encapsulated may be any water-soluble molecule with cosmetic or dermatological activity. Examples which may be mentioned are:

free-radical scavengers and/or detoxifying agents such as ascorbic acid and derivatives thereof, for instance magnesium ascorbyl phosphate, cysteine derivatives such as, for example, N-acetylcysteine, proteins, peptides and their derivatives, ubiquinone and cytochrome C, keratolytic agents such as α-hydroxy acids, β-hydroxy acids and α-keto acids, for instance salicylic acid and its derivatives, tanning accelerators such as tyrosine derivatives, depigmenting active agents such as kojic acid and arbutin and derivatives thereof, UV screening agents such as screening agents containing a sulphonic acid function, in particular 2-phenylbenzimidazole-5-sulphonic acid, sulisobenzone and benzene-1,4-bis(3-methylidene-10-camphorsulphonic acid), self-tanning active agents such as dihydroxy-acetone and indoles, liporegulators such as caffeine and theophylline, moisturizers such as sorbitol, xylitol, urea and plant DNA, antidandruff agents such as piroctone olamine and pyridinethione derivatives, optical brighteners such as stilbene derivatives and colorants such as the sodium salts of tartrazine, natural colorants extracted from plants, for instance chlorophylline, or from animals, for instance cochineal carmine, or caramel, as well as mixtures of these active principles.

The encapsulation in microcapsules according to the present invention is particularly advantageous for unstable active principles that are sensitive to various surrounding physicochemical factors such as the temperature, the pH, oxygen, the presence of oxidizing agents or of heavy metals, light or UV radiation. Specifically, encapsulation makes it possible to create a stable microenvironment which shelters the active principles from the physicochemical agents contained in or acting on the cosmetic composition.

Unstable water-soluble cosmetic or dermatological active principles which may be mentioned in particular as examples are ascorbic acid and its salts, in particular the sodium, potassium, magnesium or calcium salts.

In order to obtain a cosmetic or dermatological effect, the concentration of the active principle in the encapsulated inner aqueous phase is generally between 0.1% and 50% by weight and preferably between 5% and 25% by weight relative to the total weight of the encapsulated inner aqueous phase. It may be desirable to encapsulate relatively concentrated solutions and the upper concentration limit of the active principle is then set by the solubility limit of the active agent in the encapsulated inner aqueous phase.

The aqueous core of the microcapsules, i.e. the encapsulated inner aqueous phase of the water-in-oil primary emulsion in which the active principle is dissolved, may also contain, in dissolved form, one or more water-soluble polymers and/or one or more polyols of low molecular mass. The role of the water-soluble polymers is to stabilize the primary emulsion and/or to prevent loss of the active principle to be encapsulated from the microcapsule. The purpose of the polyols is to stabilize the active agent by reducing the water activity of the encapsulated inner aqueous phase.

The water-soluble polymers are chosen in particular from poly(vinyl alcohol), polyvinylpyrrolidone, carboxymethylcellulose, poly(carboxylic acids) and crosslinked derivatives thereof, and natural gums such as xanthans, starch, sodium alginate, pectins, chitosan, guar, carob and carrageenan. These water-soluble polymers may be present in a proportion of from 0.01% to 10% and preferably in a proportion of from 0.1% to 5% by weight relative to the total weight of the encapsulated inner aqueous phase.

The polyols of low molecular mass are chosen, for example, from glycerol and $C_2$–$C_5$ alkylene glycols, in particular propylene glycol and pentylene glycol, and may be present in a proportion of from 10% to 90% by weight and preferably in a proportion of from 10% to 50% by weight relative to the total weight of the encapsulated inner aqueous phase.

The encapsulated inner aqueous phase of the primary emulsion may also contain a salt to stabilize the primary emulsion. This salt, which is chosen, for example, from sodium chloride, potassium chloride, magnesium sulphate and magnesium chloride, is usually present in an amount of between 0.1% and 5% and preferably between 0.1% and 1% by weight relative to the total weight of the encapsulated inner aqueous phase.

Finally, the encapsulated inner aqueous phase of the primary emulsion may also contain an antioxidant.

The size and internal structure of the microcapsules depends on a large number of parameters associated with the manufacturing process, such as the temperature, the stirring speed during the emulsification, the chemical nature and respective amounts of the various water-soluble and organosoluble components, the amount of stabilizers, etc. A person skilled in the art will know how to vary these different parameters to obtain the desired microcapsule morphology.

The microcapsules may in particular be univacuolar or multivacuolar, i.e. the outer envelope may contain only one aqueous-phase compartment or alternatively the inner aqueous phase may be divided into a multitude of compartments separated by walls of the same chemical nature as the outer envelope. This phenomenon generally arises when the multiple emulsion is particularly stable and gives excellent encapsulation results.

The weight ratio of the encapsulated inner aqueous phase forming the core of the microcapsules of the present invention to the wall of these microcapsules (polymer and/or wax) is generally between 0.1/1 and 50/1 and preferably between 0.5/1 and 10/1.

The microcapsules of the present invention generally have a mean diameter of between 1 $\mu$m and 1000 $\mu$m and more particularly between 1 $\mu$m and 50 $\mu$m.

A subject of the present invention is also cosmetic or dermatological compositions containing, in a physiologically acceptable support, microcapsules with an aqueous core and with a polymeric and/or waxy envelope, as are described above.

The polymer and/or wax concentration in the cosmetic composition is in particular between 0.5% and 10% by weight and preferably between 1% and 5% by weight.

The cosmetic or dermatological compositions containing microcapsules according to the present invention may also contain adjuvants commonly used in cosmetics or dermatology, such as fatty substances, petroleum jelly, pH regulators, fragrances, preserving agents, thickeners or gelling agents, colorants, antifoams or sequestering agents.

Needless to say, a person skilled in the art will take care to select these optional additional compounds and the amount thereof such that the advantageous properties intrinsically associated with the cosmetic or dermatological composition according to the invention are not, or are not substantially, adversely affected by the addition envisaged.

The compositions according to the invention may, for example, be in the form of a serum, a lotion, an aqueous, aqueous-alcoholic or oily gel, a water-in-oil or oil-in-water emulsion, or alternatively in anhydrous form.

These compositions in particular constitute protective creams, medicated creams or care creams for the face, for the hands or the body, protective or care body milks, lotions, gels or mousses to care for or treat the skin, cleansing lotions, foundations and tinted creams, lipsticks or mascaras. In the latter cases, the composition also contains pigments.

A subject of the present invention is also a process for manufacturing microcapsules with an aqueous core containing a water-soluble active principle and with a polymeric and/or waxy envelope, as are described above. This process is a process of microencapsulation by multiple emulsion-solvent evaporation comprising the following successive steps:

(a) dissolving at least one cosmetic or dermatological active agent in an aqueous phase, (b) emulsifying the aqueous solution obtained in step (a) in a solution of at least one polymer chosen from polycaprolactone, poly(3-hydroxybutyrate), poly (ethylene adipate), cellulose esters of at least one $C_1$–$C_4$ carboxylic acid, preferably mixed cellulose esters of two types of carboxylic acid, poly(butylene adipate), copolymers of styrene and of maleic anhydride, copolymers of styrene and of acrylic acid, styrene-ethylene/butylene-styrene block terpolymers, styrene-ethylene/propylene-styrene block terpolymers and terpolymers of ethylene, of vinyl acetate and of maleic anhydride, and/or of at least one wax chosen from beeswax, polyglycerolated beeswax, hydrogenated plant oils, paraffin with a melting point above 45° C., and silicone waxes, in a water-immiscible organic solvent, (c) emulsifying the water-in-oil primary emulsion obtained in step (b) in an aqueous solution preferably containing an emulsion stabilizer, (d) removing the organic solvent by evaporation, to give an aqueous suspension of microcapsules.

The nature of the water-immiscible organic solvent used in step (b) is generally chosen as a function of its solvent power with respect to the material of the wall, its solubility in water which must be as low as possible, and its boiling point which is preferably less than 100° C. Dichloromethane, cyclohexane, heptane, 1-chlorobutane and ethyl acetate may be used, for example.

The stability of the multiple emulsion is a determining factor for obtaining good encapsulation results. Specifically, an insufficient stability of the multiple emulsion would result in mixing of the inner and outer aqueous phases and loss of the active agent from the vesicles formed. It is consequently strongly recommended to add an emulsion stabilizer to the continuous aqueous phase from step (c).

Suitable polymeric stabilizers are known in the art and may be chosen, for example, from poly(vinyl alcohol), polyvinylpyrrolidone, styrene-maleic anhydride water-soluble copolymers, carboxymethylcellulose, starch, chitosan and polyacrylic acid.

Although the use of a polymeric stabilizer is preferable, it is also possible to use water-soluble surfactants in its place.

In order to increase the stability of the multiple emulsion, the continuous aqueous phase of this emulsion may also contain from 0.1% to 10% by weight of a mineral salt chosen, for example, from sodium chloride, potassium chloride, magnesium sulphate and magnesium chloride.

A surfactant may also be introduced into the solution of organic solvent from step (b) in order to improve the stability of the primary emulsion. A person skilled in the art will know how to select the appropriate compound, such as, for example, surfactants with an HLB (hydrophilic-lipophilic balance) of less than 10, such as sorbitan esters of fatty acids like, for example, polysorbates, liposoluble lecithins, fatty acid monoglycerides, PEG-30 dipolyhydrostearate (Arlacel® P135 from the company ICI), cetyldimethicone copolyol (Abil® EM90 from the company Goldschmidt) and oxyethylenated polydimethylsiloxane (DC2-5695® from the company Dow Chemical).

The microcapsule suspension obtained after evaporating off the solvent may be used in unmodified form or may be incorporated into a cosmetic or dermatological composition.

If so desired, the microcapsules may also be separated from the aqueous suspension obtained in step (d) by filtration and may be dried so as to obtain a powder of microcapsules.

The examples which follow illustrate the encapsulation of two heat-sensitive cosmetic active agents.

EXAMPLE 1

Cytochrome C Microcapsules

An aqueous solution of cytochrome C (which may be obtained under the reference C3256 from the company Sigma) at 0.25% by weight is prepared. 5 ml of this solution are emulsified in 50 ml of dichloromethane containing 5% of cellulose acetobutyrate (CAB-381-05®, Eastman Chemical) using a homogenizer of rotor-stator type for 5 minutes while keeping the temperature below 25° C. This primary emulsion is then dispersed in 500 ml of an aqueous solution containing 1% poly(vinyl alcohol) (Rhodoviol 4-125, Rhodia Chimie), using a Moritz disperser for 20 minutes at room temperature.

The solvent of the suspension is evaporated off using a rotary evaporator (Büchi B-480) for 5 hours at 40° C., at a pressure of 75 kPa.

An aqueous suspension of microcapsules with a mean diameter of 22 µm is obtained.

The cytochrome C is assayed by UV-visible spectrophotometry at a wavelength of 506 nm.

The degree of encapsulation, i.e. the ratio of the concentration of active agent found inside the microcapsules to the total concentration of active agent, is equal to 97%. The manufacturing yield, i.e. the ratio of the amount of active agent recovered at the end of manufacturing to the amount of active agent used at the start, is equal to 100%.

The microcapsule suspension thus obtained is stored for 2 months at a temperature of 45° C. After this storage period, the loss of cytochrome C from the suspension and that of a control aqueous solution of cytochrome C having the same weight concentration of 0.25% and which has been stored under the same conditions, are measured. The results obtained are given in the table below.

EXAMPLE 2

Chlorophylline Microcapsules

An aqueous solution of chlorophylline at 0.1% by weight is prepared. 5 ml of this solution are emulsified in 50 ml of dichloromethane containing 5% of poly($\epsilon$-prolactone) (CAPA640®, Solvay) using a homogenizer of rotor-stator type for 5 minutes while keeping the temperature below 25° C. This primary emulsion is then dispersed in 500 ml of an aqueous solution containing 1% poly(vinyl alcohol) (Rhodoviol 4-125, Rhodia Chimie), using a Moritz disperser for 20 minutes at room temperature.

The solvent of the suspension is then evaporated off using a rotary evaporator (Büchi B-480) for 5 hours at 40° C., at a pressure of 75 kPa.

An aqueous suspension of microcapsules with a mean diameter of 15 µm is obtained.

The chlorophylline is assayed by UV-visible spectrophotometry at a wavelength of 405 nm.

The degree of encapsulation is equal to 90% and the manufacturing yield is equal to 100%.

The microcapsule suspension thus obtained is stored for 2 months at a temperature of 45° C. After this storage period, the loss of chlorophylline from the suspension and that of a control aqueous solution of chlorophylline having the same weight concentration of 0.1%, and which has been stored under the same conditions, are measured. The results obtained are given in the table below.

EXAMPLE 3

Ascorbic Acid Microcapsules

An aqueous solution of ascorbic acid at 5% by weight, of PH 6, is prepared. 5 ml of this solution are emulsified in 50 ml of dichloromethane containing 5% of cellulose acetopropionate (CAP-482-0.5®, Eastman Chemical) using a homogenizer of rotor-stator type for 5 minutes while keeping the temperature below 25° C. This primary emulsion is then dispersed in 500 ml of an aqueous solution containing 1% poly(vinyl alcohol) (Airvol 203®, Air Products) and 7% sodium chloride, using a Moritz disperser for 20 minutes at room temperature.

The solvent of the suspension is then evaporated off using a rotary evaporator (Büchi B-480) for 5 hours at 40° C., at a pressure of 75 kPa.

The mean size of the microcapsules obtained is 20 µm.

The ascorbic acid is assayed by HPLC in a phosphate buffer at 0.1 mol/liter, at pH 2.1, at a detection wavelength of 257 nm.

The degree of encapsulation is 85% and the manufacturing yield is 100%.

The microcapsule suspension thus obtained is stored for 2 months at a temperature of 45° C. After this storage period, the loss of ascorbic acid from the suspension and that of a control aqueous solution of ascorbic acid having the same weight concentration of 5% and also a pH of 6, and which has been stored under the same conditions, are measured. The results obtained are given in the table below.

EXAMPLE 4 (COMPARATIVE)

An aqueous solution of ascorbic acid at 10% by weight, of pH 6, is prepared. 5 ml of this solution are emulsified in 50 ml of dichloromethane containing 5% polystyrene (PM 50 000, Polysciences) using a homogenizer of rotor-stator type for 5 minutes while keeping the temperature below 25° C. This primary emulsion is then dispersed in 500 ml of an aqueous solution containing 1% poly(vinyl alcohol) (Airvol 230®, Air Products) and 7% sodium chloride, using a Moritz disperser for 20 minutes at room temperature.

The solvent of the suspension is then evaporated off using a rotary evaporator (Büchi B-480) for 5 hours at 40° C., at a pressure of 75 kPa.

The mean size of the particles obtained is 15 µm.

The ascorbic acid is assayed by HPLC in a 0.1 mol/liter phosphate buffer at pH 2.1, at a detection wavelength of 257 nm.

The degree of encapsulation is 0%, with a manufacturing yield of 100%.

EXAMPLE 5 (COMPARATIVE)

An aqueous solution of ascorbic acid at 10% by weight, of pH 6, is prepared. 5 ml of this solution are emulsified in 50 ml of dichloromethane containing 5% ethylcellulose (Ethocel® Standard FP 7 Premium, Dow Chemical) using a homogenizer of rotor-stator type for 5 minutes while keeping the temperature below 25° C. This primary emulsion is then dispersed in 500 ml of an aqueous solution containing 1% poly(vinyl alcohol) (Airvol 203®, Air Products) and 7.5% sodium chloride, using a Moritz disperser for 20 minutes at room temperature.

The solvent of the suspension is then evaporated off using a rotary evaporator (Büchi B-480) for 5 hours at 40° C., at a pressure of 75 kPa.

The mean size of the microcapsules obtained is 18 µm.

The ascorbic acid is assayed by HPLC in a 0.1 mol/liter phosphate buffer at pH 2.1, at a detection wavelength of 257 nm.

The degree of encapsulation is 17%, with a manufacturing yield of 100%.

TABLE

| | Loss of active agent after storage for 2 months at 45° C. | | |
|---|---|---|---|
| | Degree of encapsulation | encapsulated active agent | non-encapsulated control |
| Example 1 | 97% | 0% | 60% |
| Example 2 | 90% | 10% | 60% |
| Example 3 | 85% | 20% | 40% |
| Example 4 (comparative) | 0% | — | — |
| Example 5 (comparative) | 17% | — | — |

These comparative tests show the value of using a cellulose ester (Examples 1 and 3) or polycaprolactone (Example 2) instead of polystyrene (Comparative Example 4) or of a cellulose ether (Comparative Example 5) to obtain a high degree of encapsulation. Furthermore, it is found that the microcapsules of the invention make it possible to obtain better chemical stability of the cosmetic active agents included therein.

EXAMPLE 6

Tartrazine Microcapsules

An aqueous solution of tartrazine at 0.1% by weight is prepared. 5 ml of this solution are emulsified in 50 ml of dichloromethane containing 5% of a 90/10 by weight mixture of cellulose acetopropionate (CAP-482-0.5®, Eastman Chemical) and of beeswax using a homogenizer of rotor-stator type for 5 minutes while keeping the temperature below 25° C. This primary emulsion is then dispersed in 500 ml of an aqueous solution containing 1% poly(vinyl alcohol) (Airvol 203®, Air Products), using a Moritz disperser for 20 minutes at room temperature.

The solvent of the suspension is then evaporated off using a rotary evaporator (Büchi B-480) for 5 hours at 40° C., at a pressure of 75 kPa.

The mean size of the microcapsules obtained is 25 µm.

The degree of encapsulation is 98% with a manufacturing yield of 100%.

EXAMPLE 7

Day Cream Containing the Microcapsules of Example 3

| Phase A | |
|---|---|
| cetyl alcohol | 4 g |
| sorbitan tristearate | 0.9 g |
| polyethylene glycol stearate | 2 g |
| glyceryl stearate | 3 g |
| myristyl myristate | 2 g |
| octyl palmitate | 4.5 g |
| Parsol MCX ® (sold by Hoffman-Laroche) | 3 g |
| cyclopentasiloxane | 5 g |
| preserving agent | 0.1 g |
| Phase B | |
| demineralized water | 60.3 g |
| preserving agent | 0.15 g |
| sequestering agent | 0.05 g |
| Phase C | |
| powder of microcapsules of Example 3 | 15 g |

Phases A and B are heated rapidly to a temperature of 75° C. and are mixed together using a Moritz stirrer (Turbolab 2100). The emulsion is then cooled to room temperature with continued stirring, after which the powder of microcapsules (phase C) is slowly introduced therein, with gentle stirring using a Heidolph (RZR 2040) paddle stirrer.

What is claimed is:

1. Microcapsules with an aqueous core containing at least one water-soluble cosmetic or dermatological active principle, and an impermeable polymeric envelope, an impermeable waxy envelope, or an impermeable polymeric waxy envelope comprising at least one polymer selected from the group consisting of polycaprolactone, poly(3-hydroxybutyrate), poly (ethylene adipate), poly(butylene adipate), cellulose esters of at least one $C_1$–$C_4$ carboxylic acid, copolymers of styrene and maleic anhydride, copolymers of styrene and acrylic acid, styrene-ethylene/butylene-styrene block terpolymers, styrene-ethylene/propylene-styrene block terpolymers and terpolymers of ethylene, vinyl acetate and maleic anhydride, at least one wax selected from the group consisting of beeswax, polyglycerolated beeswax, hydrogenated plant oils, paraffin with a melting point above 45° C., and silicone waxes, or a combination thereof.

2. The microcapsules of claim 1, wherein the cosmetic or dermatological active principle is an unstable active principle which is sensitive to the surrounding physicochemical conditions.

3. The microcapsules of claim 2, wherein the cosmetic or dermatological active principle is selected from the group consisting of free-radical scavengers, detoxifying agents, keratolytic agents, tanning accelerators, depigmenting active agents, UV screening agents, self-tanning active agents, liporegulators, moisturizers, antidandruff agents, optical brighteners, colorants, and mixtures thereof.

4. The microcapsules of claim 3, wherein the cosmetic or dermatological active principle is ascorbic acid or a salt thereof.

5. The microcapsules of claim 1, wherein the concentration of the cosmetic or dermatological active principle in an encapsulated inner aqueous phase is between 0.1% and 50% by weight relative to the total weight of the encapsulated inner aqueous phase.

6. The microcapsules of claim 1, wherein the aqueous core further comprises one or more polyols of low molecular mass.

7. The microcapsules of claim 1, wherein the aqueous core further comprises one or more water-soluble polymers.

8. The microcapsules of claim 1, wherein the weight ratio of the encapsulated inner aqueous phase forming the core of the microcapsules to the wall of the microcapsules is between 0.1/1 and 50/1.

9. The microcapsules of claim 1, wherein the microcapsules have a mean diameter of between 1 µm and 1000 µm.

10. A cosmetic or dermatological composition comprising the microcapsules of claim 1, in a physiologically acceptable support.

11. The cosmetic or dermatological composition of claim 10, wherein the composition is in a serum, a lotion, an aqueous, aqueous-alcoholic or oily gel, a water-in-oil or oil-in-water emulsion, or anhydrous form.

12. The cosmetic or dermatological composition of claim 10, wherein the envelope is between 0.5% and 10% by weight of the cosmetic composition.

13. A process for manufacturing the microcapsules of claim 1 comprising the following successive steps:
(a) dissolving at least one cosmetic or dermatological active agent in an aqueous phase,
(b) emulsifying the aqueous solution obtained in step (a) in a solution of at least one polymer, at least one wax, or both in a water-immiscible organic solvent,
(c) emulsifying the water-in-oil primary emulsion obtained in step (b) in an aqueous solution,
(d) removing the organic solvent by evaporation so as to obtain an aqueous suspension of microcapsules,
wherein the polymers used in step (b) are selected from the group consisting of polycaprolactone, poly(3-hydroxybutyrate), poly(ethylene adipate), poly(butylene adipate), cellulose esters of at least one $C_1$–$C_4$ carboxylic acid, copolymers of styrene and maleic anhydride, copolymers of styrene and acrylic acid, styrene-ethylene/butylene-styrene block terpolymers, styrene-ethylene/propylene-styrene block terpolymers and terpolymers of ethylene, vinyl acetate and maleic anhydride, and
wherein the wax is selected from the group consisting of beeswax, polyglycerolated beeswax, hydrogenated plant oils, paraffin with a melting point above 45° C., and silicone waxes.

14. The process of claim 13, wherein the water-immiscible organic solvent used in step (b) is selected from the group consisting of dichloromethane, cyclohexane, heptane, 1-chlorobutane and ethyl acetate.

15. The process of claim 13, wherein the aqueous solution in step (c) contains an emulsion stabilizer.

16. The microcapsules of claim 1, wherein the cellulose esters are mixed cellulose esters of two types of carboxylic acid.

17. The microcapsules of claim 1, wherein the concentration of the cosmetic or dermatological active principle in an encapsulated inner aqueous phase is between 5% and 25% by weight relative to the total weight of the encapsulated inner aqueous phase.

18. The microcapsule of claim 1, wherein the weight ratio of the encapsulated inner aqueous phase forming the core of the microcapsules to the wall of the microcapsules is between 0.5/1 and 10/1.

19. The microcapsules of claim 1, wherein the microcapsules have a mean diameter of between 1 µm and 50 µm.

20. The process of claim 15, wherein the emulsion stabilizer used in step (c) is selected from the group consisting of poly(vinyl alcohol), polyvinylpyrrolidone, styrene-maleic anhydride water-soluble copolymers, carboxymethylcellulose, starch, chitosan and polyacrylic acid.

21. The microcapsules of claim 1, wherein the envelope consists of at least one of the polymers and at least one of the waxes.

22. The microcapsules of claim 1, wherein the silicone waxes are selected from the group consisting of alkyl- and alkoxydimethicones containing from 16 to 45 carbon atoms and alkyl esters of $C_{16}$–$C_{45}$ dimethiconol.

23. The microcapsules of claim 1, wherein the silicone waxes are behenoxydimethicones.

24. The microcapsules of claim 1, wherein the silicone waxes are dimethiconol behenates.

* * * * *